(12) United States Patent
Yen

(10) Patent No.: US 9,226,898 B1
(45) Date of Patent: *Jan. 5, 2016

(54) SUBMICRON PARTICLES FOR THE TREATMENT OF RADIATION DAMAGE IN PATIENTS

(76) Inventor: Richard C. K. Yen, Yorba Linda, CA (US)

( * ) Notice: Subject to any disclaimer, the term of this patent is extended or adjusted under 35 U.S.C. 154(b) by 588 days.

This patent is subject to a terminal disclaimer.

(21) Appl. No.: 12/927,543

(22) Filed: Nov. 16, 2010

Related U.S. Application Data

(60) Provisional application No. 61/281,466, filed on Nov. 18, 2009.

(51) Int. Cl.
*A61K 9/14* (2006.01)
*A61K 9/50* (2006.01)
*A61K 9/16* (2006.01)
*A61K 38/00* (2006.01)

(52) U.S. Cl.
CPC ........................................ *A61K 9/16* (2013.01)

(58) Field of Classification Search
None
See application file for complete search history.

(56) References Cited

U.S. PATENT DOCUMENTS

| | | | |
|---|---|---|---|
| 4,935,450 A * | 6/1990 | Cone, Jr. ........................ | 514/728 |
| 5,069,936 A | 12/1991 | Yen | |
| 6,262,019 B1 | 7/2001 | Keller et al. | |
| 6,264,988 B1 * | 7/2001 | Yen ................................ | 424/490 |
| 6,916,795 B1 | 7/2005 | Youssef | |
| 2002/0004522 A1 * | 1/2002 | Mueller et al. ................ | 514/431 |
| 2003/0229363 A1 * | 12/2003 | Sharkawy et al. ............. | 606/153 |
| 2005/0079132 A1 * | 4/2005 | Wang et al. .................... | 424/1.11 |
| 2008/0213370 A1 * | 9/2008 | Desai et al. .................... | 424/486 |
| 2008/0260843 A1 * | 10/2008 | Ooya et al. ..................... | 424/492 |
| 2012/0004225 A1 * | 1/2012 | Wanaski et al. ............. | 514/235.5 |

OTHER PUBLICATIONS

Drug Addiction and Anxiety (2012, updated) http://recoveryfirst.org/drug-addiction-and-anxiety.html, pp. 1-5.*
UCSF department of neurological surgery clinical programs (2012, updated) http://neurosurgery.ucsf.edu/index.php/brain_tumor_center_neuro_oncology.html, pp. 1-4.*
Sudo et al. (2001) Pulsatile Cardiopulmonary Bypass Failed to Prevent Neuropsychological Dysfunction, Ann. Thorac. Cardiovasc. Surg., vol. 7, No. 2 , pp. 89-93.*
Pignay-Demaria et al. (2003) Depression and anxiety and outcomes of coronary artery bypass surgery, Ann. Thorac. Surg., vol. 75, pp. 314-321.*

* cited by examiner

*Primary Examiner* — Anand Desai
*Assistant Examiner* — Samuel Liu
(74) *Attorney, Agent, or Firm* — David A. Guerra

(57) ABSTRACT

A method of treating a patient exposed to radiation before the patient is thrombocytopenic, comprising: intravenous infusion of protein spheres at a concentration of the protein spheres sufficient to reduce the morbidity and mortality of the irradiated patient, wherein the protein spheres are formed from soluble proteins without the addition of surfactants or detergents, and the protein spheres spontaneously and directly bind at least one coagulation factor without the aid of other molecules which specifically bind the at least one coagulation factor.

3 Claims, No Drawings

SUBMICRON PARTICLES FOR THE TREATMENT OF RADIATION DAMAGE IN PATIENTS

CROSS-REFERENCE TO RELATED APPLICATIONS

This application is a non-provisional application of and claims the benefit of priority of U.S. Provisional Application No. 61/281,466 filed on Nov. 18, 2009.

BACKGROUND OF THE INVENTION

1. Field of the Invention

The present invention relates to the field of treatment for patients, human and animal, who have been exposed to damaging doses of ionizing radiation, the treatment resulting in less morbidity or mortality.

2. Description of the Prior Art

Exposure to massive doses of ionizing radiation, such as after a dirty-bomb or atomic-bomb explosion, or a nuclear-reactor or medical radiation accident, can lead to major morbidity and/or mortality. If the victim survives the direct effect of the bomb blast, he still may suffer from damage to the nervous, digestive, pulmonary, hematopoietic and other vital systems.

Various methods have been employed to treat radiation sickness, all with limited success. For example: (1) Neumune, an androstenediol, had been used by the US Armed Forces Radiobiology Research Institute under joint development with Hollis-Eden Pharmaceuticals; (2) A Chinese herbal medicine called *Cordyceps sinensis* had been used to try to protect the bone marrow and digestion systems of mice after whole body irradiation; (3) Bisphosphonate compounds have also been tried; (4) U.S. Pat. No. 6,916,795 disclosed an "energy-protective composition" comprising adenosine phosphates; (5) Garnett and Remo disclosed at the International Symposium on Application of Enzymes in Chemical and Biological Defense, Plenary Session Abstract, May 2001 that "DNA Reductase" had some "Opportunist Clinical Activity Against Radiation Sickness"; (6) U.S. Pat. No. 6,262,019 disclosed a composition called MAXGXL which contains glytathione. All of the above are soluble enzymes, steroids or small molecules.

Of particular interest is the discussion listed under: next-bigfuture.com/2009/07/radiation-sickness-cures-and-anti.html It discussed (1) the effect of a small-molecule inhibitor to the p53-mediated apoptosis. A single shot of this drug, called CBLB502, at less than 1% of the maximum dose resulted in a 87% survival rate of mice exposed to an otherwise lethal dose of 13 Gray of radiation. By comparison, even at the maximum dose of the second-best chemical, called amifostine, only 54% of similarly irradiated mice survived. (2) The work done at the Boston University School of Medicine on new compounds called the "EUK-400 series" which may be taken orally. (3) DARPA funded work done at the Rice University called "Nanovector Trojan Horses, NTH." These carbon nanotube-based drugs may scavenge free radicals and mitigate the effects of ionizing radiation. All of the above work with mechanisms very different from the present invention.

SUMMARY OF THE INVENTION

It has been found that submicron particles can be manufactured in bulk from a number of soluble proteins, either as a single source protein or a combination of them, comprising and not limited to albumin, fibrinogen, immunoglobulin, hemoglobin, collagen and gelatin, in accordance with a previous disclosed method of manufacturing protein microspheres (U.S. Pat. No. 5,069,936 by Yen.)

It has been found that a novel manufacturing method can produce useful submicron particles, which does not involve any of the steps such as the addition of surfactants or detergents, mixing with an emulsifier, spray drying, exposure to air/liquid interface stress, heat-fixation to render the particles stable against resolubilization in vitro or in vivo. In addition, the particles produced by this novel method are essentially spherical in shape with an average diameter which is less than one micron and less than 1% of the particles are larger than one micron. The spheres will not obstruct even the smallest blood capillaries after intravenous administration and they contain no free air. Furthermore, the particles can exert their biological effects without the need to bind additional biological molecules through free functional groups such as amine, hydroxyl, carboxyl or sulfhydryl groups. The particles also do not form random clots or thrombus in the body after intravenous administration.

It has been found that the novel manufacturing methods can include a terminal sterilization step after the suspension has been sealed inside a container, such as by heat or by high hydrostatic pressure, without destroying the medical efficacy of the particles in the suspension.

It has been found consistent with the principles of rheology, that submicron particles made with the novel methods are pushed towards the walls of the blood vessels after intravenous infusion of a suspension of such small particles. Because of the proximity to the endothelium, submicron particles are able to have a profound effect on the biochemical and physiological processes of the endothelial cells. As for their distribution in the body, submicron particles are initially distributed from the site of infusion by being carried by the bulk of the fluid phase of the blood as in the case of soluble molecules. After the initial phase, these submicron particles will redistribute in a more even pattern inside the body by rolling along the walls of the blood vessels. As a result, only a very small fraction of the infused particles are recirculated to the organs responsible for the degradation of the particles, e.g. the liver; the rest remain as a layer or coating near the walls of the blood vessels. This allows a large percentage of the particles to stay in the body for prolonged periods, up to days after administration, offering prolong protective biological effects to the patient.

It has been found that the mortality rates of irradiated test animals performed in these experiments are essentially the same as published data in accordance to the radiation dose. However, infusion of a suspension of the submicron protein particles within 24 hours of exposure, or thereafter, can result in a lower mortality rate.

It has been found that about 50% of the irradiated test animals will show damage to the vital organs after being exposed to the ED50 dose of ionizing radiation, but that infusion of a suspension of the submicron protein particles within 24 hours of exposure, or thereafter, can result in less edema or damage to the vital organs, resulting in better functionality of the system.

It has been found that particles pre-coated with fibrinogen during the manufacturing process are effective in decreasing mortality and morbidity in animals irradiated with a damaging dose of ionizing radiation.

It has been found, surprisingly, that particles without pre-coating with fibrinogen or any other biologically active molecules or any intermediate molecules designed to bind biologically active molecules during the manufacturing process are also effective in decreasing mortality and morbidity in animals irradiated with a damaging dose of ionizing radiation.

It has been found that the particles may produce their medical benefits by a physical interaction such as bouncing off or rolling along the endothelium of the blood vessels.

It has been found that the particles do not appear to influence the morbidity and mortality of irradiated animals by significantly changing the rate of blood cell production or their destruction during the course of pathology progression due to the damaging dose of radiation.

It has been found that the particles produce a medical benefit without the need to know the tissue type or other laboratory values of the patient prior to administration of the particles to the patient after exposure to a damaging dose of ionizing radiation.

It has been found that the particles can be administered without harm to patients who may not have been exposed to an irreversibly damaging dose of radiation but had been in contact with other patients who had been exposed to an irreversibly damaging dose of radiation. The "potentially well" patient is uncertain about his own level of exposure and is worried; such "worried, potentially-well" patient's anxiety level and other associated symptoms can be reduced by the intravenous administration of the submicron protein particles.

Further novel features and other objects of the present invention will become apparent from the following detailed description, discussion and the appended claims.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Experiment One

Manufacture of Submicron Particles Small Enough to Remain in Suspension for Over a Year at Room Temperature Purpose:
to disclose the method of mass-production of a suspension of particles that are essentially spherical and with an average diameter of less than one micron, manufactured from a high concentration of albumin.
Material and Method:
Bovine serum albumin powder was purchased from Boval Company LP, Cleburne, Tex. and dissolved in water to result in an 18% solution. The solution will be further processed as follows without the addition of surfactants or detergents. Glutaraldehyde solution was purchased from Sigma-Aldrich, St. Louis, Mo. 63103 and diluted to 0.15 mg per ml with water. A mixture of an ethanol solution that contains glutaraldehyde, 60% to 90% ethanol with 0.5 mg. of glutaraldehyde per ml of the solution, the remainder of the solution containing water (hereafter "EG") was prepared as follows: 2850 ml of 100% ethanol USP grade was mixed with 950 ml of water, after which 7.6 ml of a glutaraldehyde solution (25%) and 114 ml of a sodium chloride solution (0.9%, USP) was added to result in 3921.6 ml of EG solution. Sorbitol powder USP grade was purchased from Sigma-Aldrich and dissolved in water to form a 25% solution. Sodium caprylate was purchased from Jost Chemical Co., St. Louis, Mo. 63114 and dissolved in water to form a 10% solution.

The following steps were done at room temperature, 19 deg to 24 deg Centigrade under sterile conditions. All the solutions were filtered via 0.2 micron filters before mixing in a class-100 clean room. At time zero, 190 ml of glutaraldehyde solution (0.15 mg/ml) was added to 381 ml of bovine serum albumin solution (18%) and well mixed in the container. Within 3 minutes, 3426 ml of EG was added and well mixed, at which time the solution turned turbid indicating the formation of spheres.

After one hour, the suspension was dialyzed in distilled water to remove the EG. After measuring the concentration of the spheres in the dialyzed suspension, sorbitol, caprylate and an additional aliquot of distilled water were added to the dialyzed suspension to result in a final concentration, respectively, of 5% sorbitol, 13.3 mg of caprylate per gram of total protein, and 8 mg of spheres/ml of suspension.

The suspension was subsequently filled into sterile containers, capped and sealed. Then the product was terminally sterilized by heating the suspension inside the container to 60 degrees Centigrade for 10 hours, or pressurized up to 600 MPa.
Results:
Analysis of the suspension showed that the particles are spherical and the median diameter was about 0.35 micron, with less than 1% of the spheres with a diameter greater than one micron. No aggregates were observed. The suspension was stable after one year of storage in room temperature without constant agitation to keep the particles in suspension. There was no significant shift of size distribution of particles after one year of storage at room temperature.

The suspension was frozen and kept frozen at minus 18 degree Centigrade for at least one year. Then samples were thawed and stored at room temperature for at least one year. Analysis of the size distribution of particles showed no significant change from the size distribution of particles in suspensions analyzed within days of completion of synthesis and terminal sterilization.
Comments:
1. Although bovine albumin solutions are used in this experiment, it is anticipated a number of other albumin solutions can be used, including human serum albumin (dialyzed in distilled water, or not dialyzed), other natural (human or animal) albumin or albumin molecules produced by recombinant-DNA methods. In addition, other proteins may be used to produce spheres with comparable functionality, including fibrinogen, immunoglobulin, collagen, gelatin, as disclosed in U.S. Pat. No. 5,069,936 by Yen.
2. Although the spheres are not further coated with any other biologically active molecules during the manufacturing process in this experiment, it is anticipated that a number of other biologically active molecules, including coagulation factors, such as fibrinogen, von Willibrand factor, Factor IX and other coagulation factors may be added to the spheres during the manufacturing process. It is expected that various ratios of mixing of the biologically active molecule solution with the sphere suspension is permissible. Specifically, experiments have been conducted where, for example, a solution of fibrinogen up to 3 mg/ml may be mixed at a ratio of 1 part (by volume) of the fibrinogen solution to 4 parts (by volume) of the sphere suspension (the turbid suspension after addition of EG, and before dialysis of the EG-containing suspension with distilled water) to result in "coated spheres." See PCT/US2008/006014 by Yen.
3. Although a specific concentration of ingredient solutions are mentioned here as an example, other higher or lower concentrations can be used when combined with a compatible compensating concentration of other ingredients. For example, albumin solutions can vary between 5% to 20% in initial concentration before the addition of a glutaraldehyde solution, which can vary from 0.05 to 0.5 mg/ml. The concentration of ethanol in the EG mix can vary from 55% to 100%, while the glutaraldehyde concentration in EG can vary from 0.1 mg to 0.75 mg/ml and the sodium chloride concentration can vary from 0.5 to 0.005 mg/ml in the EG mix.
4. It is surprising that a suspension of protein spheres can undergo heating at 60 degree Centigrade for 10 hours without forming aggregates or clumps. The addition of sorbitol together with caprylate probably has a synergistic effect on protecting the protein spheres from aggregation or expression of new antigenic sites during the process of heating and subsequent cooling to room temperature.

Experiment Two

Improvement in Mortality Rate by Treatment with Submicron Particles in Rats Irradiated with a Lethal Dose of Ionizing Radiation Purpose:

to find out if any dose of the submicron particles (not coated with any active biological molecules) can affect the mortality rate of rats exposed to a lethal dose of gamma radiation.

Material and Method:

Submicron particles were synthesized as in Experiment One without the addition of fibrinogen or any other biologically active molecules during the manufacturing steps. Test and control articles were administered intravenously to animals 24 hours after irradiation. Total body gamma-irradiation of rats is performed using a vertical beam from an AECL Eldorado therapy unit (Atomic Energy of Canada, Ltd., Commercial Products Division, Ottawa, Canada) containing a $^{60}Co$ source (1.17 and 1.33 MeV, LET=0.267 KeV/μm). Total doses of 0 Gy and 11 Gy were delivered as single fractions at a dose rate of approximately 1.5 Gy/min (γ-rays).

Results:

There were 3 groups of rats (10 rats per group): (1) irradiated rats (11 Gy) treated with normal saline (2 ml/kg, i.v.); (2) irradiated rats (11 Gy) treated with submicron particles (16 mg/kg, equal to 2 ml/kg, i.v.); (3) rats not irradiated but treated with submicron particles (16 mg/kg). The results showed that all the rats in group (3) survived to the end of the experiment with no clinical signs or ill effect, when they were sacrificed. The mortality rate of rats in group (1) was the same as expected of rats exposed to 11 Gy of radiation. The mortality rate of rats in group (2) was significantly improved compared to that of group (1).

Comments:

1. Submicron particles administered intravenously to animals exposed to lethal doses of ionizing radiation improved their survival rate. More experiments need to be done to see if a higher dose of the particles will provide further improvement, and whether given later than 24 hour after exposure to radiation will have similar protective effects.
2. Although this experiment used submicron particles not coated with fibrinogen or other biologically active molecules, it is anticipated that submicron particles pre-coated with biologically active molecules during the synthesis steps may be equally effective, or even better.
3. The exact mechanism of protection is not clear from this experiment. Given the complexity of radiation damage, it is expected that there are multiple mechanisms, each perhaps contributing in some way toward a synergistic effect. Therefore, it is expected that other products produced in a manner different from the present disclosure may be also effective in achieving the same end of improving survival rate after a massive dose of radiation. For example, products that have undergone the following steps may also be effective via mechanisms different or similar to those exerted by the presently-disclosed invention: the steps may involve the addition of surfactants or detergents, mixing with an emulsifier, spray drying, exposure to air/liquid interface stress, heat-fixation to render the particles stable against resolubilization in vitro or in vivo. In addition, particles that may not be essentially spherical in shape or with average diameter less than one micron and less than 1% of the particles being larger than one micron may also be effective. Particles containing air and particles that exert their biological effects with a requirement to bind additional biological molecules through free functional groups such as amine, hydroxyl, carboxyl or sulfhydryl groups may also be effective.

Experiment Three

Improvement of Systems Needed for Survival after Massive Radiation Exposure

Purpose:

Focus on one system, the hematopoietic system, as an indication why mortality after irradiation is improved even with delayed infusion with submicron particles.

Material and Method:

Rabbits were irradiated with 9.5 Gy to ensure failure of the bone marrow to produce an adequate concentration of platelets (see Transfusion Medicine Reviews 1997; 11:95-105). Treatment articles and control fluid were administered on day 7 after irradiation. Bleeding time were conducted on day 8 to see if any beneficial effects from test articles can last up to 24 hours after infusion.

Results:

Rabbits treated with control fluid (normal saline, 2 ml/kg) routinely have bleeding time over 800 seconds. Rabbits infused with 8 mg/kg of fibrinogen-coated submicron particles had bleeding times improved to 252 (standard deviation 75) seconds. Rabbits infused with submicron particles not coated with any biologically active molecules during production (8 mg/kg) showed bleeding times of 157 (standard deviation 33) seconds.

Comments:

1. One known mechanism of damage after radiation is the leakiness of the endothelium. Edema around the blood vessels will further decrease oxygen delivery to the tissues, leading to acute and long term damage. This experiment showed that even when submicron particles made with the present-disclosure were infused at a delay time (7 days post radiation) they remain effective in terms of at least one important system, i.e. in the control of internal (and external) bleeding. Bleeding alone may not be the major cause of death among irradiated victims, but it can weaken other systems which added together will bring about demise.

2. This experiment suggests that other systems affected by radiation: e.g. the nervous system, the digestive system, the pulmonary system, may all benefit from less leakiness of the endothelium guarding the intactness of blood vessels.
3. The benefit of infusing submicron particles may be due to a simple physical proximity to the endothelium due to the small size of the particles, by their rolling along the interior of blood vessels, or bouncing off the walls, which might have caused a certain biological responsiveness. An analogy can be found by having sand rubbed against the skin of a person: the impact may be physical, but the response is entirely physiological.
4. We expect the benefit to be short term and also long term, not only in survival rate but in less morbidity in various organ systems.
5. The data suggests that spheres not coated with fibrinogen during the manufacturing process are just as effective, in fact, better than spheres pre-coated with fibrinogen. The data point to a physical interaction of the spheres directly with the endothelium.

Experiment Four

Protection by Submicron Protein Particles Against Radiation-Induced Bleeding

Purpose:
To show that infusion of a single dose of submicron protein particles of the present invention can result in reduced Bleeding Time and improved hemoglobin concentrations in vivo.
Material and Method:
BALA/c mice (15 animals) were total-body irradiated with 7.5 Gy of gamma radiation to induce cellular damage. On post-irradiation Day 1, a single dose (8 mg/kg) of submicron fibrinogen-coated albumin spheres was injected through the tail vein, the process was completed in about 10-15 seconds. Bleeding Time (BT) and complete blood count (CBC) were performed on Day 5 in the tail vein at a location away from the initial sphere-injection site as follows: (a) a small aliquot of blood was withdrawn for CBC through a small needle, (b) after the needle was pulled from the tail vein, the same needle hole was used for the measurement of BT. BT was measured by allowing free flow of blood onto blotting paper. The time taken (in seconds) for the mouse to spontaneously stop bleeding is the value of the BT. For control, similarly irradiated mice (15 animals) were infused with an equivalent volume of normal saline. Another group of non-irradiated and non-treated mice (15 animals) were used as non-irradiated controls.
Results:
Table One shows the average value (±standard deviation) on BT (in seconds), red blood cell concentration (RBC, in $10^9$ per ml), and platelet counts (PC, in $10^6$ per ml) on Day 5 in non-irradiated and irradiated mice.

TABLE ONE

BT, RBC and PC values in mice on Day 5

|  | BT | RBC | PC |
|---|---|---|---|
| Non-irradiated control | 24.8 ± 6.7 | 6.6 ± 0.2 | 1209 ± 211 |
| Irradiated: saline control | 68.0 ± 16.2 | 5.1 ± 0.3 | 583 ± 134 |
| Irradiated: sphere treated | 44.5 ± 16.0 | 5.9 ± 0.6 | 620 ± 111 |
| P value | 0.0004 | <0.001 | 0.42 |

The data show that infusion of submicron spheres of the present invention is effective in improving the BT and RBC values of the irradiated animals. The P value is between sphere-treated irradiated mice and saline-control irradiated mice values. The data also showed that the spheres are not a growth factor and does not increase the platelet count as compared to, for example, interleukin-6 (see Patchen et al, "Administration of interleukin-6 stimulates multilineage hematopoiesis and accelerates recovery from radiation-induced hematopoietic depression" Blood, 1991, 77:472-480).
Comments:
1. Although in the present experiment albumin spheres were made from bovine serum albumin, we expect albumin spheres made from any number of sources, including dialyzed human serum albumin and non-dialyzed human serum albumin and other proteins will produce similar results.
2. Although fibrinogen-coated spheres were used in this experiment, we expect "blank" albumin spheres, not coated with fibrinogen or any coagulation factors during the manufacturing steps of the spheres will have similar results. Preliminary results presented previously have shown that blank albumin spheres made in accordance with Yen's method had the capacity of spontaneously and directly binding at least one coagulation factor from the patient's blood after infusion into the patient (see PCT/US2008/006014, "Biologic Devices for Hemostasis" by Yen).
3. Red blood cells have long half-lives in vivo. Therefore the decrease in RBC seen in the saline-treated irradiated mice 5 days after irradiation resulted mostly from spontaneous internal bleeding due to "leaky" endothelial linings of the blood vessels rat. The data suggests that the spheres of the present invention can serve as artificial platelets.
4. There can be any number of mechanisms whereby the spheres can exert a beneficial effect in irradiated patients. The following are some examples and not the only possibilities: (1) Although the spheres are not growth factors in the classical sense of soluble factors that can increase the concentration of specific cell types, the spheres may directly or indirectly stimulate the physiological responses of the endothelial cells in the peripheral blood vessels, (2) The spheres may likewise directly or indirectly stimulate the physiological responses and function of the endothelial cells in the bone marrow. Endothelial cells in the bone marrow have been observed to be associated physically and physiologically with the production of megakaryocytes and new platelets in the bone marrow. (3) The spheres may serve as pre-formed masses/solids with pre-formed surfaces that would allow a more rapid formation of a clot at a specific wound site or over internal "leaky" sites all along the endothelial linings of the vascular system, in thrombocytopenic patients as well as in patients with normal platelet counts.
5. The safety of the present invention can be traced to the fact that by themselves the spheres are inert. However, when evaluated under what is known in the normal process of clot formation, the spheres of the present invention can get trapped passively at sites where there is active formation of a clot; and only when clots are actively being formed. The normal process of a clot formation involves two important molecules: thrombin and fibrinogen. It is known that (a) at a wound site, platelets are activated, (b) prothrombin molecules from the plasma are converted into thrombin molecules in vivo on the surface of activated platelets, (c) the thrombin molecules are then bound to the surface of the activated platelets. Therefore active thrombin molecules are localized to only wound sites. The surface-associated thrombin molecules will then cleave any fibrinogen molecules that they come into contact with. These will include fibrinogen molecules on the surface of other activated platelets as well as fibrinogen molecules on the surface of the spheres. The fibrinogen molecules on the surface of the spheres can be supplied during the manufacturing process to the spheres or they can be captured from the endogenous supply of fibrinogen molecules in the plasma. Whether "blank" spheres (with no fibrinogen attached in vitro) or fibrinogen-coated spheres (with some fibrinogen added during the manufacturing process) have been administered, it is entirely conceivable that some endogenous fibrinogen will attach to the spheres (since the concentration of fibrinogen in the plasma is high, at about 2 mg/ml of plasma). Regardless of the source of the fibrinogen, once fibrinogen is cleaved, it is converted into fibrin, which will stick to other fibrin molecules to form an insoluble clot. In thrombocytopenic patients, there are not enough platelets to provide a high enough concentration of activated platelets around a wound site to form a clot quickly. With the presence of the spheres of the present invention, the total number of fibrinogen-coated particles in vivo is increased, thereby allowing the quick formation of clots (which are co-aggregates of spheres with activated platelets) at the appropriate sites. Although the effect of the spheres in the present invention is most obvious in thrombocytopenic patients, we expect a similar beneficial effect in patients who are not technically thrombocytopenic, e.g. in providing protection against radiation-induced bleeding and other radiation-induced effects.

6. The radiation dose used in this experiment is 7.5 Gy. We expect similar results when the radiation doses are even higher. We also expect a similar beneficial effect at lower lethal doses and even at sublethal doses. While sublethal doses may not cause demise of the patient, a decrease in red cell concentration will decrease the ability of the irradiated person to perform physical work and to take care of himself or help others.

7. Most of the inventor's previous disclosures concern thrombocytopenic patients. Although in this experiment, the platelet count of the irradiated animals are affected, it is expected that in situations where platelet counts may not be affected, or the effects on platelet production/consumption are not yet reflected in a lower platelet count, the spheres of the present invention can preserve the hemoglobin concentration in the patients due to its effect on increasing the integrity of the blood vessels. In such situations, it is expected that RBC values will be improved by the spheres compared to the control, regardless of the status of platelets in such patients.

Experiment Five

Other Protective and Beneficial Effects of Submicron Protein Spheres in Irradiated Patients Purpose:

To evaluate other protective and beneficial effects of the present invention in irradiated animals.

Material and Methods:

Human albumin spheres that are submicron in diameter were prepared using the method of Experiment One except that human serum albumin solutions were used instead of bovine serum albumin solutions. Four groups of mice were used: Group A and B were non-irradiated mice infused with phosphate buffered saline, or fibrinogen-coated spheres (8 mg/kg), respectively. Group C and D were mice that were subjected to total body irradiation (6 Gy) and received at 24 hours after irradiation phosphate-buffered saline, or fibrinogen-coated spheres (8 mg/kg) intravenously, respectively. The animals were euthanized on Day 51; the blood cells and spleen cells of each group were studied for significant changes compared to the other groups.

Results:

The data showed many radiation-induced changes and interaction with spheres of the present invention. Among these observed effects, the most significant changes following sphere-treatment were blood granulocytes, platelet volume and splenic oxidative burst capacity. Table Two lists the platelet volume (in $um^3$) of platelets harvested on Day 51. There is no significant difference in the platelet count among the 4 groups.

TABLE TWO

A comparison of the platelet volume in 4 groups of mice

|  | Non-irradiated, Saline-treated, group A | Non-irradiated, Sphere-treated, group B | Irradiated, Saline-treated, group C | Irradiated, Sphere-treated, group D |
|---|---|---|---|---|
| Platelet Volume | 9.51 ± 0.24 | 8.70 ± 0.26 | 8.78 + 0.22 | 9.50 + 0.22 |
| P value vs group B | <0.01 | | | |
| P value vs group C | <0.05 | NS | | |
| P value vs group D | NS | <0.05 | <0.05 | |

P values >0.05 indicate no significant (NS) difference between the two groups.

Table Three and Four lists the Reactive Oxygen Species (ROS) from spleen cells harvested on Day 51 from the 4 groups of mice. ROS are chemically-reactive molecules containing oxygen. They are highly reactive due to the presence of unpaired valence shell electrons. ROS are formed as a natural byproduct of the normal metabolism of oxygen and have important roles in cell signaling. However, during times of environmental stress (e.g. UV or heat exposure), ROS levels can increase dramatically which may result in significant damage to cell structures. This cumulates into a situation known as oxidative stress. ROS are also generated by exogenous sources such as gamma radiation used in this experiment. The data showed that in both background levels and oxidative burst, there are significant differences in the ROS of the sphere-treated group of irradiated mice against the other 3 groups.

TABLE THREE

Relative Fluorescent Units (RFU, $\times 10^3$) in background state in 4 groups of mice.

|  | Non-irradiated, Saline-treated, group A | Non-irradiated, Sphere-treated, group B | Irradiated, Saline-treated, group C | Irradiated, Sphere-treated, group D |
|---|---|---|---|---|
| Background ROS | 1.99 ± 0.30 | 2.51 ± 0.78 | 2.29 ± 0.31 | 1.01 ± 0.29 |
| P value vs group A | | NS | NS | <0.05 |
| P value vs group B | | | NS | <0.01 |
| P value vs group C | | | | <0.005 |

TABLE FOUR

Relative Fluorescent Units (RFU, $\times 10^3$) in oxidative burst in 4 groups of mice.

|  | Non-irradiated, Saline-treated, group A | Non-irradiated, Sphere-treated, group B | Irradiated, Saline-treated, group C | Irradiated, Sphere-treated, group D |
|---|---|---|---|---|
| Background ROS | 9.5 ± 1.9 | 11.9 ± 2.7 | 15.1 ± 2.8 | 5.1 ± 0.9 |
| P value vs group A |  | NS | <0.01 | NS |
| P value vs group B |  |  | NS | <0.005 |
| P value vs group C |  |  |  | <0.001 |

The data showed that irradiated mice had spleen cells that were still highly reactive on Day 51 when the mice were treated with saline on Day 1. However, the reactivity of cells were significantly reduced in irradiated mice if they were treated on Day 1 with fibrinogen-treated spheres.

Comment:

Fibrinogen-coated spheres are not growth factors and are not expected to stimulate the growth or rapid recovery of specific cell populations after irradiation or chemotherapy. However, they can have beneficial effects on the physiology of specific cell types; the effects will show up in specific biochemical reactions or responses. It is surprising that on Day 51 some cells harvested from the blood and the spleen of irradiated mice still show significant differences from their counterparts of non-irradiated mice. Of particular importance is the fact that irradiated mice treated with spheres can have values similar to that of (or better than) non-irradiated, non-treated mice, such as in the case in ROS (comparing group D with group A).

Since the beneficial effects from one dose of spheres given on Day 1 can still be detected on Day 51, a greater effect can be expected from multiple doses of sphere treatment in irradiated mice. Experiment Four showed that a single dose administered on Day 1 can reduce BT on Day 5; therefore dosing can be given every 4 days or with even greater intervals in between. Further research is also needed to evaluate if a single dose given closer to the day of irradiation (e.g. Day 4 after irradiation) is better than a single dose given on a day closer to the day when platelet counts are expected to be the lowest (e.g. Day 10-17 after irradiation). It is also possible that sphere-infusions given before the day of irradiation can have prophylactic effects. Whether spheres administered before irradiation can be more effective than spheres administered after irradiation will also need to be studied. These additional research will be most important to patients scheduled to undergo radiation therapy because the timing and dosage of radiation can be planned.

SUMMARY STATEMENTS

1. The present invention is a suspension of protein spheres that are essentially smaller than one micron in diameter, with less than 1% of the spheres at or larger than one micron. The preferred protein source is human serum albumin. The spheres are made from soluble proteins in a process without the need to add surfactants or detergents; in contrast to the prior art published by Yen and other scientists. The spheres can bind directly and spontaneously on contact with other biologically active molecules including at least one coagulation factor (including fibrinogen); whether the at least one coagulation factor is supplied as a purified source, or as plasma outside the body, or as plasma inside the body of the patient.
2. Thrombocytopenia means a deficiency in the concentration of platelets. In human beings, the normal range is 130 to $400 \times 10^6$ platelets per ml of blood. When the platelet count is 80 to $100 \times 10^6$ per ml, the condition is called mild thrombocytopenia. A platelet count of 20 to $80 \times 10^6$ per ml is typically considered moderate thrombocytopenia; while a platelet count below $20 \times 10^6$ per ml is considered severe thrombocytopenia. Most physicians will transfuse donor platelets to severely thrombocytopenic patients before they show clinical signs of bleeding. However, many moderately thrombocytopenic patients will bleed spontaneously without warning. Bleeding can include intracranial hemorrhage, which can be lethal.
3. Anemia is the condition where the red blood cells or hemoglobin concentration is abnormally low. Radiation can affect the ability of the bone marrow to produce red cells and platelets. The half life of platelets is short; therefore when production shuts down (or consumption goes up) thrombocytopenia is detected easily. Red cells have long half life in vivo; the drop in red cell concentration in the days following irradiation is due mainly to leaky blood vessels due to radiation-induced damage to the endothelium of the blood vessels: leading to spontaneous internal (multiple-site) bleeding. The present invention is effective in restoring the integrity of the endothelium, resulting in less internal blood loss compared to the control conditions which allow the internal hemorrhage to continue.
4. There may be multiple mechanisms with which the present invention exerts its beneficial effects. The spheres may directly or indirectly improve the condition of the endothelium, or they may form co-aggregates with activated platelets to form effective plugs to quickly stem bleeding. Less bleeding allows the patient to divert needed energy and the healing process to other affected vital systems, resulting in improved survival. The data presented here also suggests that infusion of the spheres of the present invention can have long term effect on lowering the abnormal responses of cells to oxidative stress, even 50 days after the administration of a single dose of the spheres.
5. The spheres of the present invention can be administered to patients before the time of irradiation, such as cancer patients scheduled to undergo radiation therapy. At this time the patient is not yet thrombocytopenic. This is in contrast to the use of spheres in the prior arts including those disclosed by Yen and other scientists where spheres are administered after the time of irradiation or are administered to thrombocytopenic patients who become thrombocytopenic due to other causes. The spheres can also be administered to patients after the exposure to radiation, such as after a nuclear event where the health problem of the patient is more than thrombocytopenia. At this time the patient will have multiple problems such as skin burn, shock, nausea, vomiting, hair loss, gastrointestinal symptoms, neurological symptoms, fever, infections, weakness etc. A single dose may be effective when given at the most appropriate time before or after the time of radiation. However, multiple doses spaced with a suitable interval in between may have a longer effective duration of action.
6. The spheres can be administered before the patient is thrombocytopenic, i.e. less than $100 \times 10^6$ per ml in platelet count. Alternatively, the spheres can be administered after the patient becomes thrombocytopenic.

7. There are many ways to measure the improvement in survival. One method is to measure the percent of survivors after a fixed number of days (e.g. 30 days) after the animals are given a fixed dose of radiation. With this method, it is possible that the sphere-treated group has a 90% survival rate on Day 30 while the placebo-treated group has a 10% survival rate on Day 30; but by Day 60 both groups have zero survival rate. Even so, treatment with the spheres will point out a path towards greater improvement. Another method of measuring survival is to measure the median length of survival of the group treated with the present invention versus that of the control group treated with placebo, after exposing both groups to the same dose of radiation. An example of this approach will be the sphere-treatment and the placebo-treatment both yield a 50% survival rate on Day 30, but the median number of days of survival in the sphere-treated group is 100 days, whereas the median number of days of survival in the placebo-group is 45 days. Such data will show superiority of the sphere-treatment over placebo-treatment or non-treatment.

8. The spheres can be administered to patients who believe that they have been exposed to radiation because of their contact with patients who have been irradiated. Recent research in "placebo effect" showed that the placebo effect can mediate through essentially the same biological pathways as the real drug effects. Therefore, the present invention can reduce the morbidity of patients whose health problems are mediated through the same pathway as patients who are in fact exposed to radiation.

9. The dosage used in these experiments are 8 mg/kg and 16 mg/kg weight of the patient. Due to the effectiveness of these spheres, it is believed that a dose as low as 0.1 mg sphere/kg administered intravenously to patients will be shown to be effective.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A method of treating an anxiolytic non-thrombocytopenic patient who is not exposed to ionizing radiations and has been in contact with irradiated patients exposed to an irreversibly damaging dose of ionizing radiation, said method comprising the steps of:
   a) providing submicron protein spheres being formed without the addition of surfactant or detergent wherein said submicron protein spheres is made by the process comprising: adding a predetermined amount of a glutaraldehyde solution to a predetermined amount of an albumin solution to form a mixture; adding an alcohol solution to said mixture to form a suspension of said submicron protein spheres, wherein said alcohol solution comprises a predetermined amount of ethanol, a predetermined amount of a second glutaraldehyde solution, and a predetermined amount of a sodium chloride solution; dialyzing said suspension in distilled water to remove said alcohol solution from said suspension; and adding caprylate and sorbitol, and distilled water to said dialyzed suspension; and
   b) administering intravenously said submicron protein spheres to said patient so as to lower abnormal responses of the patient's cells to an oxidative stress, wherein said administered submicron protein spheres are sufficient to reduce the morbidity and mortality of the non-thrombocytopenic patient who had been in contact with the irradiated patients; wherein said submicron protein spheres is capable of spontaneously and directly bind at least one coagulation factor without the aid of other molecules which specifically bind said at least one coagulation factor.

2. The method of treating an anxiolytic non-thrombocytopenic patient in accordance with claim 1 wherein over 99% of said protein spheres are smaller than 1 micron in diameter.

3. The method of treating an anxiolytic non-thrombocytopenic patient in accordance with claim 1 wherein dose for said intravenous administration of the submicron protein spheres is at least 0.1 mg of the submicron protein spheres per kilogram weight of the patient.

* * * * *